United States Patent [19]

Beschorner

[11] Patent Number: 5,597,563
[45] Date of Patent: Jan. 28, 1997

[54] METHOD INDUCTION OF ANTIGEN-SPECIFIC IMMUNE TOLERANCE

[76] Inventor: William E. Beschorner, 4310 Farmfield Ct., Baldwin, Md. 21013-9638

[21] Appl. No.: 573,648

[22] Filed: Dec. 18, 1995

Related U.S. Application Data

[63] Continuation of Ser. No. 940,640, Sep. 4, 1992, abandoned.
[51] Int. Cl.$^6$ .......................... A61K 39/00; A61K 38/22; A61K 35/28
[52] U.S. Cl. .................. 424/93.7; 424/93.21; 424/93.1; 424/93.71; 424/184.1; 424/278.1
[58] Field of Search ............................ 424/93.21, 93.7, 424/93.71, 93.1, 810, 278.1, 184.1, 185.1; 435/7.21, 7.2; 530/395, 868

[56] References Cited

PUBLICATIONS

Suppressor Cells Induced By Donor–Specific Transfusion and Deoxyspergualin In Rat Cardiac Xenografts Valdivia, et al., *Transplantation*, No. 4, 52:594–599, Oct. 1991.

Mixed Bone Marrow Reconstitution as an Approach to Xenograft Tolerance Sundt & Sachs, *National Cancer Institute*, pp. 237–246.

Improved Results With Combined Donor–Specific Transfusion (DST) and Sequential Therapy Protocol Salvatierra, et al., *Transplantation Proceedings*, No. 1, 23:1024–1026, Feb. 1991.

Olvwole et al (1988) Mechanism of Immunologic . . . Transplantation 46:352–358.

Knight et al (1986) Sensitivity of Veiles (Dendrite) . . . Transplantation 41:96–100.

Knight et al (1988) Blocking of Acquisition . . . Transplantation 46:485–535.

Roberts et al (1990) Low–Dose Immunosuppression . . . Transplantation 50:91–95.

Beschorner et al (1991, Nov.) Enhancement of Thymic Recorez . . . Transplantation 52:879–884.

Lagaais, E. L. et al., New Engl. J. Med. 321:701–5 (Sep. 14, 1989), "Effect of one–HLA–DR–Antigen–Matched and Completely HLA–DR–Mismatched Blood Transfusions on Survival of Heart and Kidney Allografts.".

Posselt, A. M., et al., Science 249:1293–1295 (14 Sep. 1990) "Induction of Donor–Specific Unresponsiveness by Intrathymic Islet Transplantation.".

*Primary Examiner*—Thomas M. Cunningham
*Attorney, Agent, or Firm*—Fish & Richardson P.C.

[57] ABSTRACT

A method for inducing antigen-specific immune tolerance by depletion of resident thymic antigen presenting cells (APCs) and re-population of thymus with new APCs containing the antigen for tolerance is described.

13 Claims, No Drawings

METHOD INDUCTION OF ANTIGEN-SPECIFIC IMMUNE TOLERANCE

This invention was made with government support under grant CA28701 awarded by the National Institutes of Health. The government has certain rights in this invention.

This is a continuation of application Ser. No. 07/940,640, filed Sep. 4, 1992, now abandoned.

BACKGROUND OF THE INVENTION

1. Field of the Invention

The present invention relates generally to the immune system and, more specifically, to a method for inducing antigen specific tolerance.

2. Description of Related Art

The host immune system provides a sophisticated defense mechanism which enables the recognition and elimination of foreign entities, such as infectious agents and neoplasms, from the body. When functioning properly, an effective immune system distinguishes between foreign invaders and the host's own tissues. The ability to specifically ignore the host's own tissues is called immune tolerance. Immune tolerance to self normally develops at birth when self antigens are brought to the thymus by antigen presenting cells (APCs). Thus, APCs play a crucial role in the "programming" of the immune system by specifically indicating which antigens are not to be considered foreign and, thereby, tolerated by the immune system. Autoimmune disease occurs when there is a breakdown in immune tolerance which results in a loss of tolerance to a particular antigen(s) and a subsequent attack by the host's immune system on the host's tissues which express the antigen(s). Immune tolerance to self is considered to be T cell dependent. Thus, the thymus plays a central role in the development of self tolerance. The antigen specificity of immune tolerance is determined by antigens presented by APCs. During the development of neonatal tolerance, these APCs migrate readily to the thymus and through their interaction with other cells of the immune system establish which antigens will be considered "self" and, thereby, will be sheltered from attack by the immune system. In the adult, the primary blood born antigen presenting cells are dendritic cells (DC), which localize at the corticomedullary junction of the thymus. Adoptive transfer of thymus explants has supported suggestions that these cells determine the antigen specificity of tolerance (Suzuki, et al., *J. Immunol.*, 142:1463, 1989).

The ability of the immune system to distinguish between self and foreign antigens also plays a critical role in the area of tissue transplantation. The success of a transplant depends on preventing the immune system of the host recipient from recognizing the transplant as foreign and, in some cases, preventing the graft from recognizing the host tissues as foreign. For example, when a host receives a bone marrow transplant, the transplanted bone marrow may recognize the new host as foreign, resulting in graft versus host disease (GVHD). Consequently, the survival of the host depends on preventing both the rejection of the donor bone marrow as well as rejection of the host by the graft immune reaction.

At present, deleterious immune reactions are prevented or treated by general immune suppression in that the suppression is not antigen specific. Nonspecific immune suppression agents, such as steroids and antibodies to lymphocytes, put the host at increased risk for infection and development of tumors. In recent years, unwanted immune reactions have been prevented or treated with more selective immune suppression, such as with Cyclosporine A (CsA). CsA was thought to inhibit the proliferation of cytotoxic T cells while having relatively little effect on the proliferation of suppressor T cells. In addition, immunosuppressive therapy with CsA leads to depletion of the thymic medullary dendritic cells, the principal antigen presenting cells of the adult thymus. Although CsA has significantly improved the overall success of transplants and has shown some success with autoimmune diseases, it must be administered for the life of the patient. As a result, patients receiving such long-term CsA therapy are constantly at considerable risk for infections and neoplasms, as well as toxicity from the CsA.

Unwanted immune reactions which can result in autoimmune disease and transplant rejection can also be inhibited using steroids, azathioprine, anti-T cell antibodies, and more recently, monoclonal antibodies to T cell subpopulations. In addition to CsA, other selective immunosuppressive drugs that have been used include rapamycin, desoxyspergualine, and FK506. Unfortunately, when such agents are withdrawn, the unwanted immune reactions often recur. Ideally, it is a primary goal of transplantation immunology to achieve immune tolerance in an antigen-specific manner such that the unwanted immune reaction is prevented without inducing a state of generalized immune deficiency and accompanying increased susceptibility to disease. As a result, the tolerant host would remain capable of reacting appropriately to other antigens such as those associated with life-threatening infections or neoplasms.

Because of the major drawbacks associated with existing immunosupressive modalities, there is a need for a new approach for inducing immune tolerance in the host. The present invention provides such a novel method which allows antigen-specific tolerance while eliminating the need for protracted immunosuppressant therapy by utilizing a brief immunosuppressive treatment, just long enough to induce depletion of thymic medullary dendritic cells and allow recruitment of new APCs to the thymus. New antigen presenting cells containing the antigen to which specific tolerance is desired can be infused simultaneously or shortly thereafter. Since most individuals have only a limited capacity to regenerate the thymus, thymic regeneration can be stimulated by human growth hormone (hGH), human insulin-like growth factor-1 (hIGF-1), or related agents, after infusion of antigen presenting cells.

It has been known since 1967 that a connection exists between the anterior pituitary and the immune system, and specifically with growth hormone (GH). Two groups of investigators concluded from their studies that GH controls the growth of lymphold tissue (Pierpaoli and Sorkin, *Nature*, 215:834, 1967; Baroni, *Experientia*, 23:282, 1967). Subsequently, immunologic function was restored in the pituitary dwarf mouse by a combination of bovine somatotropic hormone and thyroxin (Baroni, et al., Immunol., 17:303–314, 1969).

In a sex-linked dwarf chicken strain, bovine GH (bGH) treatment resulted in enhanced antibody responses and bursal growth while thyroxine treatment stimulated thymus growth (Marsh, et al., *Proc. Soc. Exp. Biol. Med.*, 175:351–360, 1984). However, neither treatment altered immune function in the autosomal dwarf chicken. Bovine GH therapy alone partially restored immunologic function in immunodeficient Weimaraner dogs (Roth, et al., *Ann. J. Vet. Res.*, 45:1151–1155, 1984).

Studies have shown that mice with hereditary GH deficiency develop an impairment of the immune system associated with thymic atrophy, immunodeficiency, and wasting, resulting in a shortened life expectancy (Frabris, et al., *Clin. Exp. Immunol.*, 9:209–225, 1971 ). It has been shown that an age-associated decline in the plasma concentration of thymulin (a thymic hormone) occurs and that plasma thymulin concentration increases in bGH-treated middle-aged and old dogs (Goff, et al., *Clin. Exp. Immunol.*, 68:580–587, 1987). The authors suggest that exogenous GH may be useful for restoring some immune functions in aged individuals. Further, administration of hGH to $C_{57}/B1/6J$ mice was found to reverse the inhibitory effect of prednisolone on thymus and spleen cellularity and on natural killer activity; administration of hGH without prednisolone had no effect, although at higher doses it induced a decrease of thymic parameters and natural killer activity with no effect on spleen cellularity, and relative weights (Franco, et al., *Acta Endocrinologica*, 123:339–344, 1990).

It has also been shown that GH induces T-cell proliferation in the thymus (Murphy, et al., *FASEB Meeting Abstract*, Atlanta, April 1991; Durum, et al., *FASEB Meeting Abstract*, Atlanta, April 1991). For recent reviews on the immune effects of GH, see Kelley, "Growth Hormone in Immunobiology," in *Psychoneuroimmunology II*, 2nd Ed., B. Ader, et al., eds., Acad. Press 1990, and Ammann, "Growth Hormone and Immunity," in *Human Growth Hormone Progress and Challenges*, L. Underwood, ed., Marcel Dekker, Inc., New York (1988), pp. 243–253; Weigent and Blalock, *Prog. NeuroEndocrinImmunology*, 3:231–241 (1990). It has been reported that all major immune cell types, including T-cells, B-cells, natural killer (NK) cells and macrophages, can be activated or expanded by GH (Kelly, *Biochem. Pharmacol.*, 3.8:705, 1989).

One report states that locally generated IGF-I mediates GH action on T-lymphocytes through the type 1 IGF receptor (Geffner, et al., *J. Clin. Endocrin. and Metab.*, 71:464, 1990). Also, Franco, et al., on p. 343, speculate that some of the effects of hGH on the immune system occur via IGF-I. Timsit, et al. (*73rd Annual Meeting, Endocrine Society*, June 19–22, 1991, abstract 1296) report that hGH and IGF-I stimulate thymic hormone function.

In addition, there have been data published documenting the ability of cells of the immune system to produce IGF-I-like molecules. These include activated alveolar macrophages (Rom, et al., *J. Clin. Invest.*, 82:1685, 1988), human B-lymphocytes transformed with Epstein-Barr virus (Merimee, et al., *J. Clin. Endocrin. Metab.*, 69:978, 1989), spleen and thymus tissues through detection of mRNA for IGF-I (Murphy, et al., *Endocrinology*, 120:1279, 1987), and normal T-cells (Geffner, et al., supra).

Data have also been presented suggesting that IGF-I produced locally in tissues such as the thymus or inflammatory sites might affect the growth and function of IGF-I-receptor-bearing T-lymphocytes (Tapson, et al., *J. Clin. Invest.*, 82:950–957, 1988).

A statistically significant increase in thymus and spleen weight of hypophyscentomized rats infused for 18 days with IGF-I was observed as compared to control or treatment with GH (Froesch, et al., *Growth Hormone Basic and Clinical Aspects*, eds. O. Isaksson, et al., p. 321–326, 1987). Also reported was an increased thymic tissue in young GH-deficient rats treated with IGF-I (Guler, et al., *Proc. Natl. Acad. Sci. USA*, 85:4889–4893, 1988)) and an increase in the spleen of dwarf rats (Skottner, et al., *Endocrinology*, supra). Others have shown repopulation of the atrophied thymus in diabetic rats using either IGF-I or insulin; however, when the rats were immunized with bovine serum albumin (BSA) and boosted, serum anti-BSA antibodies showed no effect of insulin or IGF-I on the antibody response despite large effects on thymic and splenic size (Binz, et al., *Proc. Natl. Acad. Sci. (USA)*, 87:3690–3694, 1990). IGF-I was reported to stimulate lymphocyte proliferation (Johnson, et al., *Endocrine Society 73rd Annual Meeting*, abstract 1073, Jun. 19–22, 1991).

Furthermore, IGF-I was found to repopulate the bone marrow cavity with hematopoietic cells (Froesch, et al., supra), stimulate erythropoiesis in hypophysectomized rats (Kurtz, et al., *Proc. Natl. Acad. Sci. (USA)*, 85:7825–7829, 1988), and enhance the maturation of morphologically recognizable granulocytic and erythroid progenitors in suspension cultures of marrow cells (Merchav, et al., *J. Clin. Invest.*, 81:791, 1988).

At nanomolar concentrations, IGF-I is a growth-promoting factor for lymphocytes (Schimpff, et al., *Acta Endocrnol.*, 102:21–25, 1983). B-cells, but not T-cells, have recently been shown to possess receptors for IGF-I (Stuart, et al., *J. Clinical Endo. and Met.*, 72:1117–1122, 1991). Also, IGF-I, as a chemotactic factor for resting and activated T-cells, stimulates an increase in thymidine incorporation into resting and activated T-cells. Normal T-cell lines show augmentation of basal colony formation in response to IGF-I (Geffner, et al., supra). It is also stated on p. 955 of Tapson, et al. (*J. Clin. Invest.*, 82:950–957, 1988) that IGF-I produced locally in tissues, such as the thymus or inflammatory sites, might affect the growth and function of IGF-I receptor-bearing T-lymphocytes. However, IGF-I is reported to suppress in a dose-dependent manner IL-2-induced proliferative responses and in vitro antibody 15 responses of splenocytes (Hunt and Eardley, *J. Immunol.*, 136:3991–3999, 1986).

SUMMARY OF THE INVENTION

The present invention relates to a method of inducing antigen-specific tolerance in an animal. More specifically, the method entails treatment of an animal with an immunosuppressant agent under conditions sufficient to deplete the thymic medulla, or thymic equivalent, of antigen presenting cells, followed by infusion of dendritic cells which are tolerogenic for the antigen. Preferably, the animal is also administered a thymus regenerating agent, such as growth hormone or insulin-like growth factor −1.

In so doing, the present invention achieves the long sought goal of inducing antigen-specific tolerance while minimizing risk to the animal that is normally associated with protracted immunosuppressive therapy. The invention achieves this previously elusive goal by, in essence, re-programming the immune system of the animal to recognize a new repertoire of self antigen and, thereby achieves immune tolerance for the antigen. Thus, the invention is fundamentally different from existing therapies which rely upon immune suppression.

DETAILED DESCRIPTION

The present invention provides a novel method for inducing tolerance to an antigen by administering to a recipient an enriched population of antigen presenting cells (APCs) tolerogenic for the antigen, in combination with the antigen. In situations where transplantation of donor tissue is the goal, the tolerogenic APC's are presented with the donor tissue. Alternatively, tolerance may be restored to self antigens in patients with autoimmune diseases. When the loss of self-tolerance results from a thymus unable to maintain tolerance because of insufficient APCs, then the thymus can be regenerated with recruitment of additional APCs from the patient. If the loss of self-tolerance results from defective antigen presenting cells, then either new APCs can be infused or the host's APCs (or corresponding precursor cells) can be harvested and modified before reinfusing into the patient. An immunosuppressant agent is administered substantially contemporaneously with the APCs under conditions which deplete the thymic medulla of dendritic cells and induce tolerance. Additionally, to accelerate thymic recovery, a thymus regenerating agent can be administered subsequent to APC and immunosuppressant treatment.

A preferred element of the present invention is that the immunosuppressive agent is administered for only a relatively short period of time. The agent should be administered for a period of time long enough to deplete the thymic medulla of those APCs, such as dendritic cells, which are present at the beginning of therapy and is preferably withdrawn before the thymic medulla is repopulated with new APCs which induce tolerance for the antigen. By withdrawing the immunosuppressive agent at this time, deleterious effects of the agent on the new APCs are minimized.

The minimum preferred appropriate time at which to withdraw the immunosuppressive agent can be ascertained by monitoring the appearance of cortical thymocytes outside the thymus, for example, in the peripheral blood, lymph node, or spleen. Cortical thymocytes are relatively undifferentiated and possess both the $CD4^+$ and $CD8^+$ markers. Under normal conditions, cortical thymocytes are found primarily in the thymus, consequently most thymocytes in the peripheral blood are more differentiated and are typically either $CD4^+$ or $CD8^+$, but not both $CD4^+$ and $CD8^+$. Since the ability of the cortical thymocytes to be released from the thymus into the peripheral blood is directly related to the depletion of dendritic cells from the medulla of the thymus, it is possible to follow the effect of immunosuppressant therapy on dendritic cell depletion by monitoring cortical thymocyte levels in peripheral blood. For example, by using commonly available antibodies to the $CD4^+$ and $CD8^+$ markers, it is possible to detect those cells which have both markers, for example, by using a cell sorter. By definition such cells are primarily cortical thymocytes. Cortical thymocytes could also be monitored by analyzing peripheral lymphocytes that are $CD1^+$.

As used herein, "tolerance to an antigen" refers to unresponsiveness to an antigen without inducing a prolonged generalized immune deficiency. Consequently, according to the invention, a tolerant host is capable of reacting to other antigens. Tolerance represents an induced depression in the response of an animal that, had it not been subjected to the tolerance-inducing procedure, would be competent to mount an immune response to that antigen.

As used herein, "antigen" refers to a substance which elicits an immune response. The antigens of the invention to which tolerance is induced may or may not be exogenously derived relative to the host. For example, the method of the invention may be used to induce tolerance to an "autoantigen". An autoantigen is a normal constituent of the body that reacts with an autoantibody. The invention also includes inducing tolerance to an "alloantigen". Alloantigen refers to an antigen found only in some members of a species, for example the blood group substances. An allograft is a graft to a genetically different member of the same species. Allografts are rejected by virtue of the immunological response of T lymphocytes to histocompatibility antigens. The method of the invention also provides for inducing tolerance to a "xenoantigen". Xenoantigens are substances which cause an immune reaction due to differences between different species. Thus, a xenograft is a graft from a member of one species to a member of a different species. Xenografts are usually rejected within a few days by antibodies and cytotoxic T lymphocytes to histocompatibility antigens.

The method of the invention is useful for preventing an immune reaction to transplanted organs from other human donors (allografts) or from other species such as sheep, pigs, or non-human primates (xenografts), for example. Such tissues for transplant include, but are not limited to, heart, liver, kidney, lung, pancreas, pancreatic islets, brain tissue, cornea, bone, intestine, skin, and hematopoietic cells. The method of the invention is useful in preventing graft versus host disease in cases of mismatched bone marrow or lymphoid tissue transplanted for the treatment of acute leukemia, aplastic anemia, and enzyme or immune deficiencies, for example.

The method of the invention is also useful for treatment of autoimmune diseases where the immune system attacks the host's own tissues. Such autoimmune diseases include, but are not limited to, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitic, leukocyte adhesion deficiency, rheumatoid arthritis, rheumatic fever, Reiter's syndrome, psoriatic arthritis, progressive systemic sclerosis, primary biniary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, autoimmune complications of AIDS, atrophic gastritis, ankylosing spondylitis and Addison's disease.

The recipient animal of the invention includes rodents, pigs, cats, dogs, chickens, sheep, cattle, non-human primates and most preferably humans. As used herein, "antigen presenting cell" refers to accessory cells or non-lymphocytic cells, such as dendritic cells, Langerhans cells, and mononuclear phagocytes that help in the induction of an immune response by presenting antigen to helper T lymphocytes. B lymphocytes can assume the function of accessory cells in antigen presentation. The antigen presenting cell of the invention is preferably a dendritic cell. APCs of the invention may be isolated from the bone marrow, blood, thymus, epidermis, liver, fetal liver, or the spleen, for example.

The method of the invention comprises administering to a recipient an enriched antigen presenting cell population "in combination with the antigen". In combination with the antigen refers to the process whereby a cell presents antigen on its surface in a form capable of being recognized by a T lymphocyte or thymocyte. The antigen must be associated with either class II (for presentation to helper T cell), Class I (for presentation to cytotoxic T cells), or Class III histocompatibility molecules that are also present on the cell surface. Because of extensive polymorphisms, the presented antigen may be an integral component of the histocompatibility molecule. In the method of the invention, the antigen or tolerogen is present on the surface of the dendritic cell, for example. In the case of a transplant or graft, dendritic cells are harvested from the donor and presented to the recipient host substantially contemporaneously with the transplant tissue.

In an autoimmune disease, the immune tolerance system of the patient fails to recognize self antigens and, as a consequence of this loss of tolerance, brings the force of the immune system to bear on tissues which express the antigen. According to the method of the invention, a patient with autoimmune disease is treated with the immunosuppressive agent as described herein to deplete the thymic medulla of resident APCs, such as dendritic cells, then, preferably, the immunosuppressive agent is withdrawn. Following withdrawal of the immunosuppressive agent, APCs from other regions of the patient's body which are tolerogenic for the self antigens previously targeted by the autoimmune disease re-populate the thymus and restore immunologic homeostasis by regulating autoimmune reactions and arrest the autoimmune disease. If the loss of self-tolerance results from defective APCs, then either new APCs could be infused or the host's APCs (or corresponding precursor cells) could be harvested and modified before reinfusing into the patient. For example, genetic engineering could replace an HLA-DQ known to be defective in inducing tolerance with an acceptable HLA-DQ. In this situation, the new or altered APCs would be infused at the end of administration of the immunosuppressive agent. In each situation, the recruitment of DC into the thymus could be enhanced by administering a thymus regenerating agent.

As used herein, the term "enriched" as applied to the APC population of the invention refers to a substantially homogeneous population of APCs which are substantially free from other cells with which they are naturally associated. An enriched population of APCs can be achieved by several methods known in the art. For example, an enriched population of dendritic cells can be obtained using immunoaffinity chromatography using monoclonal antibodies specific for determinants found only on dendritic cells.

Enriched populations can also be obtained from mixed cell suspensions by positive selection (collecting only the desired cells) or negative selection (removing the undesirable cells). The technology for capturing specific cells on affinity materials is well known in the art (Wigzel, et al., *J. Exp. Med.*, 128:23, 1969; Mage, et al., *J. Immunol. Meth.*, 15:47, 1977; Wysocki, et al., *Proc. Natl. Acad. Sci. USA*, 75:2844, 1978; Schrempf-Decker, et al., *J. Immunol Meth.*, 32:285, 1980; Muller-Sieburg, et al., *Cell*, 44:653, 1986).

Monoclonal antibodies against antigens specific for mature, differentiated cells have been used in a variety of negative selection strategies to remove undesired cells, for example, to deplete T cells or malignant cells from allogeneic or autologous marrow grafts, respectively (Gee, et al., *J.N.C.I.* 80:154, 1988). Purification of human hematopoietic cells by negative selection with monoclonal antibodies and immunomagnetic microspheres can be accomplished using multiple monoclonal antibodies (Griffin, et al., *Blood*, 63:904, 1984). Enriched dendritic cell composition can be obtained from a mixture of lymphocytes, since dendritic cells lack surface Ig or T cell markers and do not respond to B or T cell mitogens in vitro. Dendritic cells also fail to react with MAC-1 monoclonal antibody, which reacts with all macrophages. Therefore, MAC-1 antibodies provide a means of negative selection for dendritic cells.

Procedures for separation of cells may include magnetic separation, using antibody-coated magnetic beads, affinity chromatography, cytotoxic agents joined to a monoclonal antibody or used in conjunction with a monoclonal antibody, for example, complement and cytotoxins, and "panning" with antibody attached to a solid matrix, for example, plate, or other convenient technique. Techniques providing accurate separation include fluorescence activated cell sorters, which can have varying degrees of sophistication, for example, a plurality of color channels, low angle and obtuse light scattering detecting channels, impedance channels, etc.

The immunosuppressive agent used according to the method of the invention is an agent which depletes the thymic medulla of APCs, such as dendritic cells. A preferred immunosuppressant of the invention is Cyclosporine A (CsA), however other agents which cause immune suppression by depletion of thymic medulla dendritic cells, such as rapamycin, desoxyspergualine, and FK506 or functional equivalents of these compounds may also be utilized. CsA is preferably administered by injection at a dose from about 0.3 to about 50 mg/kg/day, preferably from about 2.5 mg/kg/day to about 10 mg/kg/day. The duration of CsA treatment may range from about 2 to about 20 days, preferably about 14 days.

The immunosupressive agent is administered by any suitable means, including parenteral, subcutaneous, intrapulmonary, and intranasal administration, and if desired for local immunosuppressive treatment, intralesional administration (including perfusing or otherwise contacting the graft with the immunosuppressive agent prior to transplantation). Parenteral infusions include intramuscular, intravenous, intraarterial, or intraperitoneal administration. In addition, the immunosuppressive agent is suitably administered by pulse infusion, particularly with declining doses of the immunosuppressive agent. Preferably, the dosing is given by injections, most preferably intravenous or subcutaneous injections, depending in part on whether the administration is brief or chronic.

Advantageously, other suitable immunosuppressive agents can be readily identified by a simple in vivo screening technique which is based on monitoring cortical thymocyte levels outside the thymus, such as in the peripheral blood. As mentioned above, the immunosuppressive agents of the invention induce depletion of resident medullary APCs, such as dendritic cells, from the thymus. Physiologically, one role of these cells is to act in a "barrier-like" manner between the cortex and the medullary regions of the thymus. In this role, these cells prevent the transit of immature conical thymocytes from the cortex out of the thymus. However, upon depletion of the APCs from the medulla this barrier function becomes impaired and, as a result, cortical thymocytes appear in extra-thymic regions, such as the peripheral blood. Thus, it is possible to monitor the effectiveness of an immunosuppressive agent of the invention simply, for example, by detecting the increase of $CD1^+$ or $CD4^+8^+$ thymocytes in peripheral blood. By monitoring $CD1^+$ or $CD4^+8^+$ thymocyte levels outside the thymus, it is possible to reasonably estimate when the immunosuppressive agent has sufficiently depleted the thymus of resident APCs and immunosuppressive therapy can be withdrawn. Animal models for testing various immunosuppressive agents using this screen are well known to those of skill in the art (Hess, et al., *Transplant Proc.*, 19:2683, 1987).

As used herein, "substantially contemporaneously" refers to the time at which the immunosuppressant is administered to the recipient in relation to the time at which the APCs are administered. For example, a heart transplant recipient may receive enriched dendritic cells derived from donor spleen, during transplant surgery and receive CsA for a short time immediately following for about 10–16 days, preferably about 14 days. These donor dendritic cells are able to induce tolerance to donor antigens carried on the surface of the dendritic cell. The donor dendritic cells will re-populate the thymus of the recipient host and re-program the host T-cells to be tolerant of donor antigens of the donor heart. In general, where transplant grafts are involved, the immunosuppressive agent can be administered from about 1 day to about 90 days before infusion of the tolerogenic APCs until about 7 days to about 90 days after the infusion of tolerogenic APCs. Preferably, the immunosuppressive agent is administered from about 7 days to about 28 days before infusion of tolerogenic APCs until about 7 days to about 28 days after infusion of tolerogenic APCs. Where autoimmune disease is treated by infusion of foreign or altered tolerogenic APCs, administration of immunosuppressive agent parallels the treatment times described for transplant grafts. Alternatively, where the treatment of the autoimmune disease relies upon re-population of the thymic medulla with the patient's own APCs, the immunosuppressive agent is administred for about 3 days to about 6 months, more preferably, from about 7 days to about 28 days.

According to the invention, an allogeneic bone marrow transplant recipient may have his own bone marrow harvested, and processed to obtain a composition of enriched dendritic cells before transplant of the donor bone marrow. The patient may receive immunosuppressive therapy followed by the infusion of transplanted bone marrow and dendritic cell composition previously harvested from the patient's own bone marrow.

In most cases, after the recipient has been treated with an immunosuppressant and APCs containing antigen, a thymic regeneration agent may be administered. However, although administration of such agent is preferred, it is not necessarily required to practice the invention. These regeneration agents act by accelerating the recovery of the thymus, inducing proliferation and activation of T cells, and recruiting APCs into the thymic medulla. Such agents include, but are not limited to, human growth hormone (hGH) and somatomedins, such as insulin-like growth factor-1 (IGF-1) and insulin-like growth factor-2 (IGF-2). hGH is given at a dose from about 0.01 mg/kg/day to about 10.0 mg/kg/day, preferably from about 0.1 mg/kg/day to about 5 mg/kg/day. IGF-1 is administered from about 0.1 mg/kg/day to about 15.0 mg/kg/day, and preferably from about 0.1 mg/kg/day to about 5.0 mg/kg/day. hGH and IGF-1 are given for a period of time which allows recruitment and proliferation of APCs to the thymic medulla. This may range in duration from about 3 to about 20 days, preferably about 14 days.

The regeneration agent is administered by any suitable means, including parenteral, subcutaneous, intrapulmonary, and intranasal administration. Parenteral infusions include intramuscular, intravenous, intraarterial, or intraperitoneal administration. In addition, the regeneration agent is suitably administered by pulse infusion, particularly with declining doses of the regeneration agent. Preferably, the dosing is given by injections, most preferably intravenous or subcutaneous injections, depending in part on whether the administration is brief or prolonged.

Other thymic regeneration agents for use according to the invention can be identified by monitoring the level of $CD4^+8^+$ cortical thymocytes as described above for immunosuppressive agents. The difference is that a useful regeneration agent will result in a decrease in the number of extra-thymic $CD4^+8^+$ cortical thymocytes in, for example, peripheral blood.

Enriched APCs are administered in a physiologically acceptable solution. Preparations of enriched APCs for parenteral administration include sterile aqueous or non-aqueous solutions, suspensions, and emulsions. Examples of non-aqueous solvents are propylene glycol, and polyethylene glycol. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

The following examples are intended to illustrate, but not limit the invention. While they are typical of those that might be used, other procedures known to those skilled in the art may alternatively be used.

EXAMPLE 1

Experimental Methods

Animals. Virus antibody-free female Lewis rats (RT1) were purchased from Charles River Co. (Wilmington, Mass.). The rats were approximately 7 weeks old (130–150 g) at the start of the study. Experimental groups consisted of four to six animals each.

Administration of CsA, recombinant human growth hormone (rhGH), and recombinant human insulin-like growth factor 1 (rhIGF-1). CsA (Sandoz, Inc., Basel, Switzerland) was dissolved in absolute ethanol (15% weight/volume), and a stock solution diluted 1:20 in sterile saline and 2% Emufior (Kodak). Rats received 15 mg/kg/day CsA subcutaneously for 14 days. For comparison, normal untreated, age-related LEW female rats were examined. CsA-treated rats were sacrificed at the end of the CsA treatment, and complete autopsies performed.

The remaining CsA-treated rats were injected with either rhGH, rhIGF-1, or vehicle for 21 days. Recombinant human growth hormone (Eli Lilly, Indianapolis, Ind.) was dissolved in sterile saline and injected daily for 21 days (500 µg/kg/day, s.c.). Recombinant human insulin-like growth factor 1 (Eli Lilly, Indianapolis, Ind.) was dissolved in 0.1M acetic acid (pH 1.9) just prior to injection (2 mg/kg/day, s.c.). The vehicle group consisted of injections of the rhIGF-1 vehicle.

Autopsies. Complete autopsies were performed on the above-described five groups. The animals were weighed and examined for evidence of infection or autoimmune disease. The thymus and spleen weights were taken. Half of the thymus and part of the spleen were frozen for immunoperoxidase procedures.

A cell suspension was made from a small portion of the thymus for flow cytometry. The remainder of the thymus and spleen as well as other tissues were fixed in neutral-buffered formalin. Hematoxylin and eosin stains were performed.

Immunoperoxidase stains. The avidin-biotin complex method of immunoperoxidase staining (Beschorner et al., *Am. J. Pathol.*, 126:487, 1987) was used to localize and determine the relative number of various cell markers in the thymus. The primary monoclonal antibodies included anti-ED1 (Bioproducts for Science, Indianapolis, IN), anti-OX6 for class II antigen, W3/25 for CD4, and anti-OX8 for CD8. Intermediate thymocytes were detected in tissue by staining for terminal deoxynucleotidyl transferase (TdT) using a rabbit antibody to calf TdT (Supertechs MD., Bethesda, Md. [DiPrimio, et al., *Hematol. Pathol.*, 1:173, 1987]). Sections stained for TdT were fixed previously with paraformaldehyde. Cytokeratin was detected for enumerating the number of Hassall's corpuscles using a polyclonal rabbit antibody to 56 and 64 kD cytokeratin.

Histomorphometry. Computerized planimetry was performed using the Video Image Analysis System (VIAS). This system superimposes the observed microscopic field on a digital pad. As the cursor traces the perimeter of the cortex and medulla, the corresponding X, Y coordinates are analyzed by the computer. Three to 6 thymic lobules per animal were scored for each parameter evaluated, depending on the size of the thymic section.

Anti-ED1 (Sminia, et al., *Thymus*, 8:141, 1986) stains both dendritic and nondendritic macrophages. Under the conditions employed here, the dendritic cells (DC) were readily distinguished from macrophages and occasional stained endothelial cell. Only those with multiple, clearly apparent dendritic processes were scored.

The parameters determined by computerized planimetry included the cortical and medullary areas, and the number of ED1 positive dendritic cells within the cortex and medulla. The medullary and cortical dendritic cell densities, respectively, were calculated by dividing the dendritic cell count obtained for the medulla or the cortex by the overall lobular area (cortex plus medulla). The relative medullary area was generated from the ratio of medullary to lobular areas. Hassall's corpuscles were enumerated using sections stained for cytokeratin. The Hassall's corpuscles were recognized as intensely stained concentric layers of epithelium. Over all, medullary epithelium was compared between groups by comparing and ranking the sections from greatest to least. Class I and class II antigens were evaluated on sections stained from anti-$OX_{18}$ and anti-OX6, respectively. The antigen expression was compared using the rank-file system. The slides were ranked according to overall expression, cortical expression, medullary expression, and expression in the deep cortex adjacent to the medulla.

Class II antigen expression in the deep cortex adjacent to the medulla was quantified using VIAS. In the normal thymus, most of the surface of the medulla is in contact with deep cortical cells expressing class II antigen. Only focal regions adjacent to the medulla do not express class II antigen. The total perimeter of each medullary region was measured as well as the total length of medulla in contact with class II antigenopositive deep cortex. The ratio of length of contact to perimeter was used as an estimate of the relative surface area of contact with cortical class II antigen with medulla.

Analytical flow cytometry. Two-color flow cytometry, using monoclonal antibodies to CD4 (W3/25) and CD8 (OXB), determined the relative numbers of single-labeled $CD4^+$ and $CD8^+$ lymphocytes as well as double-labeled $CD4^+/CD8^+$ cells. Single-cell suspensions of thymus were made, and the viability was determined with trypan blue. The cells were stained at 4° C. with FITC-labeled anti-W3/25 and biotinylated anti-OX8. After thorough washing, the cells were then incubated with avidin-phycoerythrin. The cell suspensions were analyzed with a FACScan flow cytometer (Becton Dickinson, San Jose, Calif.) and FACScan research software. Acquisition gates were set to exclude cellular debris. For analysis, gates were set using the forward and side-scatter profiles.

Statistical analysis. The means of parametric values were compared between experimental groups using the Student's t test with a $P<0.05$ considered significant. Nonparametric analyses were compared using the Wilcoxon-Mann-Whitney two-sample test, with $P<0.05$ considered significant.

EXAMPLE 2

Effect of rhGH and rhIGF-1 on the Weight of the Thymus and Spleen

Twenty-one days after stopping cyclosporine, both rhGH and rhIGF-1 induced a significant enlargement of thymus, 30% greater than the vehicle-treated rats (Table 1). This was significantly greater than the increase in body weight. In contrast, the increase in splenic weight paralleled the body weight.

TABLE 1

| | | | Thymus | | Spleen | |
|---|---|---|---|---|---|---|
| Treatment | n | Body Weight | Grams | % Body Weight | Grams | % Body Weight |
| Vehicle | 6 | 164 ± 18 | 0.38 ± 0.03 | 0.23 ± 0.02 | 0.36 ± 0.02 | 0.22 ± 0.02 |
| GH | 5 | 183 ± 7[a] | 0.50 ± 0.04[b] | 0.27 ± 0.02[c] | 0.41 ± 0.02[c] | 0.22 ± 0.01 |
| IGF-1 | 6 | 182 ± 9 | 0.49 ± 0.03[b] | 0.27 ± 0.01[c] | 0.43 ± 0.02[b] | 0.24 ± 0.01 |

THYMUS AND SPLEEN WEIGHTS, 21 DAYS AFTER CsA

[a] $P < 0.05$; vs vehicle.
[b] $P < 0.0005$; Student's t test vs vehicle.
[c] $P < 0.02$; vs vehicle.

Table 2 summarizes the CD4 and CD8 phenotypes of the thymus. At the completion of the CsA, there was a significant increase in double-labeled cells and a decreased number of $CD4^+$ single-labeled cells. By 21 days, the relative numbers of mature (total single labeled) and immature (double labeled) thymocytes were close to that in normal rats. However, the vehicle-treated rats still had a relative predominance of $CD8^+$ cells among the mature thymocytes. Rats treated with either rhGH or rhIGF-1, however, showed a significant increase in $CD4^+$ lymphocytes and a significant decrease in $CD8^+$ single-labeled lymphocytes. In both groups the profile and CD4/CD8 ratio more nearly approximated the normal rats.

TABLE 2

| | n | CD4[a] | CD8[b] | CD4/CD8 | 4/8 ratio |
|---|---|---|---|---|---|
| THYMOCYTE PHENOTYES 21 DAYS AFTER CsA | | | | | |
| Normal | 6 | 17.5 ± 6% | 14.0 ± 5% | 64.0 ± 6% | 1.20 |
| End of CsA | 6 | 1.7 ± 7% | 19.5 ± 3.8% | 77.9 ± 4.4% | 0.09 ± 0.04 |
| 21 Days after CsA | | | | | |
| Vehicle | 6 | 10.8 ± 1.4% | 21.9 ± 3.3% | 59.8 ± 5.2% | 0.50 ± 0.09 |
| GH | 5 | 15.8 ± 2.3% | 16.5 ± 3.9% | 58.0 ± 7.1% | 0.85 ± 0.12[a] |
| IGF-1 | 6 | 15.4 ± 1.9% | 16.1 ± 3.1% | 61.4 ± 6.2% | 0.96 ± 0.10[a] |

[a]$P < 0.002$; Student's t test vs vehicle.
[b]$P < 0.05\%$; vs vehicle.

The morphometric analysis is summarized in Table 3. Three weeks after CsA, the vehicle-treated rats showed partial regeneration of the thymus with respect to Hassall's corpuscles, medullary area, and medullary dendritic cells.

Both rhGH- and rhIGF-1-treated rats displayed increased Hassall's corpuscles compared with the vehicle-treated rats. While the vehicle-treated rats demonstrated a diffuse distribution of single epithelial cells, the rhGH- and rhIGF-1-treated rats showed coalescence of the epithelium in the outer portion of the medulla, similar to that observed in normal rats. When this feature was analyzed by rank-file analysis, the difference between either the rhGH or rhIGF-1 group and the vehicle group was significant ($P=0.02$ and $P=0.01$, respectively, Wilcoxson-Mann-Whitney test).

TABLE 3

MORPHOMETRIC ANALYSIS OF THE THYMUS 21 DAYS AFTER CsA

| | Hassal's corpuscles | Medullary Area % of | DENDRITIC CELLS[a] | |
|---|---|---|---|---|
| | HC/7 lobules | lobule | Medullary | Cortical |
| Normal Rats | 11.4 ± 4.9 | 22.6 ± 4.9 | 269.4 ± 28.9 | 278.4 ± 46.5 |
| End of CsA | 0.5 ± 0.8 | 0.5 ± 0.5 | 13.3 ± 12.2 | 243.1 ± 125 |
| 21 Days Post CsA | | | | |
| Vehicle | 4.5 ± 0.4 | 10.9 ± 2.1 | 142.9 ± 7.3 | 276.0 ± 63.7 |
| rhGH | 7.0 ± 2.0[a] | 9.9 ± 4.0 | 172.7 ± 52.1 | 319.3 ± 105.0 |
| rhIGF-1 | 7.8 ± 2.0[b] | 16.9 ± 3.8[b] | 186.4 ± 34.0[a] | 229.9 ± 67.8 |

[a]$P < 0.05$; Student's t test vs vehicle
[b]$P < 0.01$; Student's t test vs vehicle
[c]Number of cells/mm The class II antigen expression of the three groups was significantly less than the normal control rats ($P<0.05$, Wilcoxon-Mann-Whitney test), with respect to overall expression, cortical expression, medullary expression, and deep cortical expression. There was no significant difference in the overall, cortical, or medullary expression between the 3 treatment groups at 21 days post-CsA.

However, the deep cortical expression, as measured by the relative medullary surface area in contact with class II antigen-positive cortex, was moderately but significantly increased in the rats treated with rhGH (Table 4). The rh IGF-1-treatment group showed a trend toward greater expression.

TABLE 4

DEEP CORTICAL CLASS II MHC EXPRESSION

| | n | % of medulla in contact with cortical class II antigen |
|---|---|---|
| Normal rats | 4 | 83.4 ± 8.0 |
| End of CsA | 6 | 20.0 ± 7.7 |
| 21 days post-CsA | | |
| Vehicle | 5 | 50.8 ± 3.4 |
| rhGH | 5 | 62.9 ± 7.2[a] |
| rhIGF-1 | 5 | 58.2 ± 6.7[b] |

[a]$P < 0.01$; Student's t test vs vehicle.
[b]$P = 0.06$; Student's t test vs vehicle.

EXAMPLE 3

Recruitment of New Dendritic Cells Into the Thymic Medulla During Thymic Regeneration The medullary dendritic cells within the medulla and at the corticomedullary junction are responsible for the antigen specificity of thymus dependent tolerance. In order to induce tolerance to antigens, therefore, new DC must be recruited to this region. The normal thymus is resistant to the recruitment of new DC. It was hypothesized that DC may be recruited during the regeneration of the thymus following Cyclosporine treatment. In these studies, the recruitment of new DC was traced by injecting LEWxBN ($F_1$=LBN) DC and DC precursor cells into BN rats. The LBN cells were later identified by immunoperoxidase stains using a mono clonal antibody (HIS 19) that reacts with the LEW class II antigen, but not the BN antigen.

Young (six week) female (BN) RT1.N rats were treated with Cyclosporine (15 mg/kg/day, sc) or vehicle for 14 days. Dendritic cells were provided from multiple different sources of LBN rats. The BN recipients were then sacrificed at 0 to 42 days after stopping the CsA or vehicle. Sections of the thymus and spleen were frozen. They were stained with the mouse monoclonal antibody, HIS19, followed by biotinylated horse anti-mouse immunoglobulin and avidin-biotin complex. The immunoperoxidase stains were developed with diaminobenzidine substrate and hydrogen peroxide, followed by copper sulfate, and counterstained with Giemsa stain.

The dendritic cells from the LBN rats were treated in several ways. Spleen cells ($3 \times 10^7$ per rat) were injected into the recipients either at the beginning of CsA (or vehicle) or at the end of the CsA (or vehicle). Because the dendritic cells are resistant to radiation, irradiated spleen cells (2000 R) were also injected at the end of CsA. Langerhans cells in the skin are phenotypically similar to the thymic dendritic cells. Therefore, 3-2 cm LBN skin grafts were placed on BN recipients either at the beginning of CsA or at the end of CsA.

When normal LBN spleen cells were injected into vehicle treated BN rats, numerous dendritic cells were apparent within the spleen at three days after injection. The thymus, in contrast, showed no dendritic cells at any time point. By ten days post injection, the spleen LBN cells were rejected and were no longer evident.

In contrast, when LBN cells were injected at the end of CsA, the DC were numerous in both of the thymus and spleen at three days. By ten days the thymic DC had localized within the medulla and the corticomedullary region. By 21 days post injection, the DC were reduced, but still present within the thymic medulla.

Significantly better recruitment of LBN cells was observed when the spleen cells were injected at the beginning of CsA. A sequential study of the thymus showed an absence of LBN DC at day zero, but numerous medullary DC at day 10. The spleen, in contrast, showed LBN DC at both day zero and day ten.

When irradiated spleen cells were used as a source of DC, recruitment was also observed within the thymic medulla. However, the kinetics differed from the use of normal spleen cells. When irradiated LBN cells were injected at the end of CsA relatively few thymic DC were observed at day 10. At day 21 post injection, DC were numerous and were still quite apparent at 42 days post injection.

Recruitment of LBN cells from the skin grafts was also observed, with localization within the thymic medulla at day 10. This was seen whether the skin grafts were placed at the beginning or end of CsA therapy. Examination of the thymus at the end of CsA demonstrated no apparent LBN cells, although they were quite evident within the spleen. Again, this indicated that the recruitment occurred during the regeneration of the thymus after stopping CsA.

These sequential experiments demonstrated that new DC are recruited into the thymic medulla after stopping CsA. This is during a period of rapid regeneration of the thymus. Of particular note, the DC are not recruited into the thymus during CsA treatment. There is also no entry of DC into a normal thymus that is not undergoing rapid growth or regeneration.

The LBN cells are antigenically distinct from the recipient (BN). They therefore could be rejected just as any other allograft. The resistance of the thymus to recruitment of new DC, however, is not simply a function of rejection. Even at the early time points when numerous LBN cells are recruited into the normal spleen, no LBN DC were evident within the normal thymus.

Although growth factors were not used in these particular studies, the young rats that were used normally demonstrate a rapid regeneration of the thymus after CsA, most likely due to the endogenous presence of growth factors. A principal point of these studies is that the dendritic cells responsible for the antigen specificity of tolerance can be recruited into the thymus under conditions of thymic and thymic medullary growth.

EXAMPLE 4

The Use of Growth Factors to Enhance Thymic Regeneration and Recruitment of Thymic DC After Long-Term CsA Under prior art therapeutic modalities, patients with organ or bone marrow transplants or with autoimmune diseases are typically treated with low dose Cyclosporine for the rest of their lives. This example shows the ability of long-term CsA therapy to prevent thymic regeneration, and tests the ability of growth factors (recombinant human insulin-like growth factor 1 (rhIGF-1)) to enhance the regeneration of the thymus after long-term CsA.

LEW rats (six weeks, female) were treated with CsA (7.5 mg/kg/day, sc) for up to four months. At the end of the CsA, rats received either vehicle or rhIGF-1 (1.5 mg/kg/day, ip, via Alzet 2002 pump) for two weeks. These rats were then sacrificed four weeks after stopping the CsA. The rats as well as the thymus and spleen were weighed. The frozen sections of thymus and spleen were stained for rat dendritic cells using the monoclonal antibody ED1. The number of medullary dendritic cells per thymic globule were determined using computerized image analysis.

After four months of CsA, the thymuses weighed an average of 0.25±0.05 gm. Control rats (treated for two weeks with vehicle) sacrificed four weeks later had thymuses that weighed essentially the same (0.26±0.06 gm). In contrast, the rats treated with rhIGF-1 after four months of CsA had thymuses that averaged 0.33±0.2 gm (P<0.01 vs vehicle; Table 5).

TABLE 5

USE OF GROWTH FACTORS TO ENHANCE THYMIC REGENERATION AND RECRUITMENT OF THYMIC DC AFTER LONG-TERM CsA

| TREATMENT | THYMUS WEIGHT[a] | MEDULLARY DC PER LOBULE |
|---|---|---|
| 4 mos. CsA | 0.25 ± 0.05 | 70 |
| 4 mos. CsA + Vehicle | 0.26 ± 0.06 | 180 ± 49 |
| 4 mos. CsA + rhIGF-1 | 0.33 ± 0.02[b] | 313 ± 109[c] |

[a]grams
[b]P < 0.01 vs vehicle, P < 0.05 vs end of CsA
[c]P < 0.025 vs vehicle, P < 0.01 vs end of CsA These studies demonstrate that growth factors enhance the regeneration of the thymus or thymic equivalent under conditions in which the involuted thymus is resistant to regeneration. More importantly, the growth factor was able to enhance the recruitment of new DC which are responsible for the antigen specificity of tolerance. In these studies, the DC were from the host and are responsible for re-establishment of self-tolerance. This indicated that under conditions enhancing the immune system, these growth factors could ameliorate autoimmune diseases when used with the appropriate dendritic cells.

EXAMPLE 5

Reconstitution of the Thymic Medullary Microenvironment Leads to Regulation and Suppression of Autoimmune Reactions and Autoimmune Disease Autoimmune diseases, such as type 1 diabetes mellitus, autoimmune thyroiditis, rheumatoid arthritis, scleroderma, primary biliary cirrhosis, Sjögren's syndrome, etc., result from immune components, including lymphocytes and antibodies, that react with and injure the patient's tissues.

A model of CsA induced autoimmune disease was studied using LEW marrow injected into lethally irradiated LEW rats. The recipient was then treated with CsA. One to two weeks after stopping the CsA, the rats developed a GVHD-like syndrome which rapidly progressed into chronic GVHD. Clinically, the chronic GVHD resembled scleroderma (progressive systemic sclerosis), with additional features of primary biliary cirrhosis, and Sjögren's syndrome.

Two experimental variables which were considered important in this model included the presence of the thymus and irradiation to the thymic region prior to CsA. If the thymus was removed before CsA, animals did not develop the autoimmune disease. Normally animals that had not received mediastinal or thymic irradiation also did not develop the autoimmune disease. CsA has been shown to interfere with negative selection in the thymus (Jenkins, et al., Science, 241:1655, 1988). Therefore, self-reactive thymocytes can escape the thymus during CsA and cause the injury responsible for the autoimmune disease. (This is not observed during CsA therapy because the immunosuppressive effects of CsA prevent the self-reactive T cells from destroying the tissues).

Conditions that permitted the full recovery of the thymus also prevented the development of the autoimmune disease. In contrast, when the thymus was removed at the end of CsA, the autoimmune disease routinely developed shortly thereafter. (Beschorner, et al., Transplantation, 52:688, 1991)

Enhancing the immune system by stimulating the regeneration of the thymus or thymic equivalent induced tolerance to self. This example shows that tolerance to self was reestablished by the proliferation and maturation of suppressor T cells.

EXAMPLE 6

Thymic Regeneration with Host DC Prevents Graft-Vs-Host Disease in Allogeneic Bone Marrow Recipients Allogeneic bone marrow transplantation is the treatment of choice for hematologic malignancies, aplastic anemia, and many enzyme and immune deficiencies. It could also be used for the treatment of solid malignancies such as breast carcinoma. The principal complication of allogeneic bone marrow transplantation is graft-vs-host disease. Among those who survive the initial phase, chronic graft-vs-host disease is a frequent complication, with many features of autoimmune diseases.

In this example, mismatched bone marrow transplants in rats were used to test the effect of dendritic cells after CsA and the effect of growth factor on the development of acute or chronic GVHD. Eight week old female LEW (RT1.1) rats were given total body irradiation (1020R). Twenty-four hours later they received $6 \times 10^7$ ACI (RT1.a) bone marrow cells. Following the transplant, one group received vehicle while the other three groups received CsA (15 mg/kg/day) for 14 days, One of the CsA treated groups received nothing following the CsA. A second group received $3-10^7$ LEW bone marrow cells at the end of CsA while the third group received $3 \times 10^7$ LEW bone marrow cells followed by two weeks of rhIGF-1 (1.5 mg/kg/day, sc).

At 37 days post-transplant, all rats were evaluated for histologic evidence of cutaneous GVHD. At 97 days post-transplant, the remaining surviving rats were sacrificed and histologic evidence of GVHD evaluated at autopsy. Results are shown in Table 6.

TABLE 6

Development of GVHD in Allogeneic Bone Marrow Recipients

| Group | Immuno-suppressive | Lew Post-Cs/t Infusion | Growth Factor | Post-Transplant Severe GVHD (%) 37d | 97d |
|---|---|---|---|---|---|
| 1 | vehicle | None | None | 75 | N.A.[c] |
| 2 | CsA[a] | None | None | 65 | 75 |
| 3 | CsA[a] | $3 \times 10^7$ | None | 0 | 0[d] |
| 4 | CsA[a] | $3 \times 10^7$ | TGF-1[b] | 0 | 0[e] |

[a]15 mg/kg/day for 14 days
[b]1.5 mg/kg/day for 14 days
[c]None of the Group 1 animals survived to day 97
[d]30% survival rate
[e]75% survival rate In the vehicle treated group, 75% developed severe acute GVHD by 37 days post-transplant; none survived to 97 days. The second group receiving CsA but no LEW bone marrow after CsA developed severe acute or chronic GVHD in 65% of the animals at 37 days. In the two groups receiving LEW bone marrow cells following CsA, none of the chimeras developed severe or chronic GVHD. The group receiving rhIGF-1 demonstrated better survival at 97 days (75%) compared to the group receiving bone marrow, but no rhIGF-1 (30%).

The first two groups reflect typical problems after bone marrow transplantation. Untreated recipients typically develop acute GVHD. Patients treated with CsA show a high incidence of chronic GVHD resembling autoimmune diseases.

Normally, one of skill in the art would expect an additional antigen load to enhance the GVHD. Instead, it was surprisingly found that when LEW bone marrow cells were injected after CsA, both acute and chronic GVHD was prevented. Because the cells were injected after withdrawal of CsA, it is unlikely that the tolerance resulted from a selective immunosuppressive action of the CsA, but rather, it is more likely that the tolerance resulted from APC being recruited into the thymus or thymic equivalent.

Although both groups given LEW cells post CsA (Groups 3 and 4) showed an absence of GVHD, the group that received growth factor had a greater long term survival. This is consistent with an improved immune reconstitution, thereby placing the recipient at a decreased risk for infection. Thus, specific tolerance of the injected donor bone marrow cells to the host was induced, while at the same time the immune reconstitution was enhanced.

EXAMPLE 7

Thumic Regeneration With Donor DC Prolongs Survival of Skin Allografts

The standard method for preventing rejection of solid organ allografts such as heart, kidney, liver, pancreatic islet, and intestinal allografts is to chronically suppress the immune system. Typical immunosuppressive agents include prednisone, azathioprine (IMURAN), and CsA. Chronic immune suppression, however, subjects the patient to an increased risk for infection and malignancy. This example shows that conditions which enhance the immune system, in a manner that also stimulates the development of antigen specific tolerance, actually prolongs skin allograft survival.

The recipient strain rats (6–8 week, female, LEW or BN) were treated with 14 days of CsA (15 mg/kg/day, sc). The control group then received dendritic cells from the skin graft donor strain followed by 14 days of vehicle. The experimental group received the same dendritic cells plus rhIGF-1 (1.5 mg/kg/day, Alzet 2002 pump). At 3 to 5 weeks following the end of CsA, 2 cm skin grafts were placed on the back of these animals. The skin grafts included the grafts from the recipient strain, from the DC donor strain, and from a third party strain. The skin grafts were followed and evaluated every other day. The median survival time (MST) for each of the experimental groups was then determined for each strain of graff.

Table 7 summarizes three separate experiments that compare skin allograft survival in rats treated with CsA and donor DC with rats treated with CsA, donor PC, and rhIGF-1. The results demonstrate that under conditions that enhance the immune system, i.e., enhancement of thymic regeneration with rhIGF-1, the skin grafts survive longer.

TABLE 7

PROLONGATION OF RAT ALLOGENEIC SKIN GRAFT SURVIVAL WITH POST-CSA rhIGF-1

| | Skin Graft | | | MST[a] | | |
|---|---|---|---|---|---|---|
| Exp | Donor | Recipient | Donor DC | Control Group[b] | Test Group[c] | P < |
| 1 | ACI | LEW | Marrow + Skin | 10 (n = 7) | 22 (n = 4) | .03 |
| 2 | LEW | BN | Spleen (LBN) | 13 (n = 6) | 22 (n = 9) | .05 |
| 3 | ACI | LEW | Skin | 19 (n = 9) | 27 (n = 9) | .03 |

[a]Median survival time of allografts in days
[b]CsA + DC
[c]CsA + DC + rhIGF

Although a significant prolongation was noted for each of the skin grafts corresponding to the post-CsA DC, there was no significant prolongation of third party skin graft survival. Thus, the tolerance that was induced was antigen specific.

Experiment 3 was part of a larger study. In that study it was demonstrated that both enhancement of thymic regeneration and dendritic cells were essential for prolongation of the skin graff survival. When rhIGF-1 was administered without the DC, there was no prolongation of skin graff survival. When splenic DC were injected without subsequent growth factor, there also was no prolongation of skin graff survival. Similarly, temporary skin grafts placed without the rhIGF-1 also had no effect on subsequent survival.

Skin graff survival is generally considered the most stringent test of organ allograft rejection. In particular, the donor→recipient combinations tested here (ACI→LEW and LEW→BN) normally require considerable immune suppression to prolong the survival of the graft.

It should be noted that the test grafts were placed 3 to 5 weeks after withdrawal of CsA. Thus, the prolongation was not simply a function of residual CsA. Indeed, if there were residual immune deficiency from the previous CsA treatment, the group receiving the growth factor would be expected to have much more immune competence and a decreased immune deficiency. Thus, if skin graft survival were only a function of residual CsA induced immune deficiency, then the rhIGF-1 treated rats would have been expected to have a shorter survival, not longer as was found according to the invention.

Based on the existing body of knowledge in the field of transplantation, the effect of the method of the invention on other grafts, such as heart and kidney grafts, would be much more profound than seen with the skin grafts tested here, since the survival of skin grafts is much more difficult to achieve.

The results observed with the allografts also suggest that transplants of xenografts would also be successful.

Although the invention has been described with reference to the presently preferred embodiment, it should be understood that various be made without departing from the spirit of the invention. Accordingly, the invention is limited only by the following claims.

I claim:

1. A method of inducing at least partial tolerance to an alloantigen comprising:

administering to a recipient animal a dendritic cell depleting amount of an immunosuppressive agent, for a time and under conditions sufficient for depletion of the dendritic cells in the recipient's thymic medulla;

administering to the recipient animal a tolerogenic, amount of an intraspecies dendritic cell population in combination with the antigen, substantially contemporaneously with the immunosuppressive agent wherein the intraspecies dendritic cell population is enriched with intraspecies dendritic cells tolerogenic for the antigen and the administering is under conditions sufficient to repopulate the recipient's dendritic cell-depleted thymic medulla; and administering a thymic regeneration agent for a time and under conditions sufficient to induce recruitment of dendritic cells to the thymus, wherein the thymic regenerating agent is administered following the immunosuppressive agent and simultaneously or following administration of dendritic cells.

2. The method of claim 1, wherein the thymic regeneration agent is a growth factor.

3. The method of claim 2, wherein the growth factor is growth hormone.

4. The method of claim 2, wherein the growth factor is a somatomedin.

5. The method of claim 4, wherein the somatomedin is insulin-like growth factor-1.

6. The method of claim 1, wherein the recipient is a human.

7. The method of claim 1, wherein the APCs tolerogenic for the antigen are of dendritic cell lineage.

8. The method of claim 1, wherein the APCs tolerogenic for the antigen are derived from the same animal as the antigen.

9. The method of claim 8, wherein the APCs tolerogenic for the antigen are of splenic, bone marrow, blood, thymus, epidermal, liver, or fetal liver origin.

10. The method of claim 1, wherein the immunosuppressive agent is selected from the group consisting of cyclosporine, desoxyspergualine, rapamycin and FK506.

11. The method of claim 1, wherein the antigen is an alloantigen.

12. The method of claim 1, wherein the antigen is a xenoantigen.

13. The method of claim 1, wherein the antigen is an autoantigen.

* * * * *